United States Patent [19]

Peterson

[11] 4,308,817

[45] Jan. 5, 1982

[54] STATE OF CHARGE BATTERY MONITOR

[75] Inventor: Francis C. Peterson, St. Charles, Ill.

[73] Assignee: Illinois Tool Works Inc., Chicago, Ill.

[21] Appl. No.: 179,595

[22] Filed: Aug. 19, 1980

[51] Int. Cl.³ ..................... G01F 23/02; H01M 31/04
[52] U.S. Cl. ..................................... 116/215; 429/90; 429/91
[58] Field of Search ................. 116/215, 200; 73/327, 73/441; 429/90, 91

[56] References Cited

U.S. PATENT DOCUMENTS

| | | | |
|---|---|---|---|
| 2,132,923 | 10/1938 | Beck | 116/215 |
| 3,647,641 | 3/1972 | Grubb et al. | 429/90 |
| 3,893,339 | 7/1975 | Melone | 73/327 |
| 3,895,964 | 7/1975 | Sakamoto | 429/91 |
| 4,074,025 | 2/1978 | Miyagawa | 429/91 |
| 4,203,065 | 5/1980 | Whitford | 429/90 |

FOREIGN PATENT DOCUMENTS 55-12631 1/1980 Japan .

*Primary Examiner*—Robert I. Smith
*Attorney, Agent, or Firm*—Jerold M. Forsberg; T. W. Buckman

[57] ABSTRACT

There is disclosed a monitor for monitoring the state of charge of a battery having an internal charge transfer medium. A monitor includes detecting means arranged to be disposed beneath the surface of the charge transfer medium and arranged for sensing the specific gravity of a fluid medium, enclosure means for enclosing the detecting means, and a fluid medium within the enclosure means. The fluid medium exhibits specific gravities related to the degree of electric charge therein and the enclosure means is formed at least partly from a non-permeable electric charge transmissible material to enable the fluid medium to assume the electric charge of the charge transfer medium while substantially separating the fluid medium therefrom. The monitor further includes indicating means responsive to the detecting means for indicating the specific gravity of the fluid medium and thus the state of charge of the battery.

20 Claims, 6 Drawing Figures

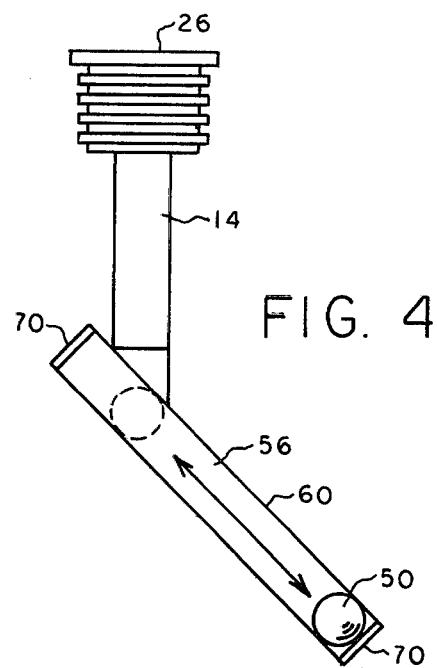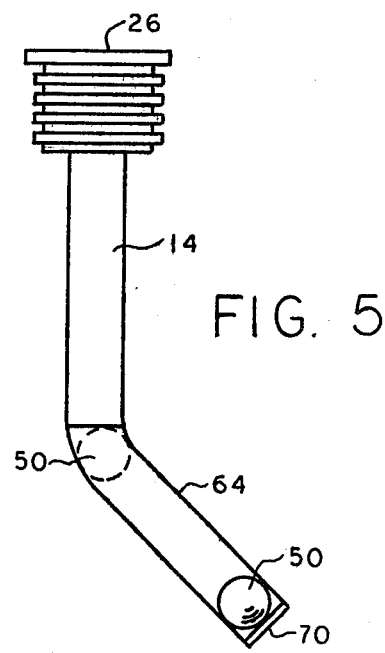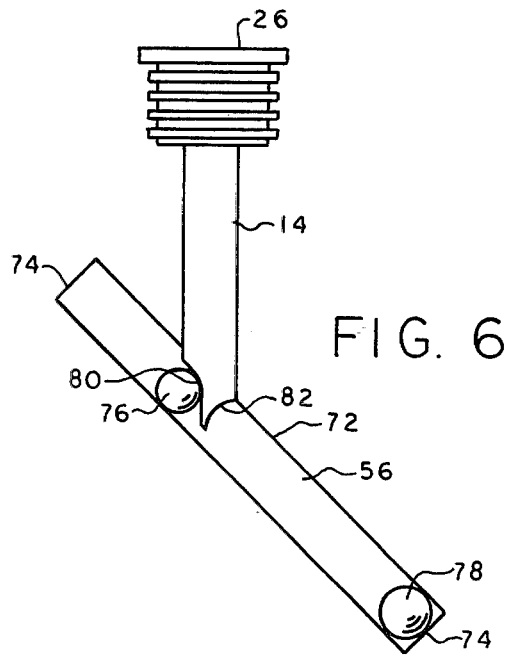

STATE OF CHARGE BATTERY MONITOR

BACKGROUND OF THE INVENTION

The present invention is generally directed to battery indicating devices and more particularly to a new and improved monitor for monitoring the state of charge of a battery having virtually any type of electrolyte.

In any system wherein one or more storage batteries are utilized it is often desirable, if not essential, to be able to monitor the state of charge of the battery or batteries. In the case of the well known lead-acid type storage battery commonly used in automobiles, it has been found that the most accurate and reliable method of determining the state of battery charge is to measure the specific gravity of the sulfuric acid electrolyte. The specific gravity of the sulfuric acid decreases with decreasing charge therein. As a result, the specific gravity decreases to a point which indicates that the battery requires recharging.

This relationship between electrolyte specific gravity and battery charge has been utilized to advantage in many prior art devices for monitoring charge. For example, U.S. Pat. Nos. 3,597,973 and 3,893,339 which are assigned to the assignee of the present invention fully show and describe such devices. As disclosed therein, the devices include a light transmissive member having an external indicating surface and a reflecting surface adapted to be submerged in the liquid electrolyte. A cage or chamber is connected to the light transmissive member and confines a float member therein having a predetermined density. The light transmissive member is aligned with the chamber and the float member is movable relative to the reflecting surface for indicating the specific gravity of the liquid electrolyte. In one position, the float member is in the bottom of the chamber out of view of the light transmissive member and thus cannot be seen at the external indicating surface. This informs the user that the electrolyte specific gravity is below a predetermined value and that recharging is necessary. In another position, a float member is at an upper portion of the chamber aligned with the light transmissive member and is viewable at the external indicating surface. This informs the user that the specific gravity of the electrolyte is above the predetermined value and that the battery's state of charge is such that recharging of the battery is not necessary.

Battery monitors of this type have found wide acceptance for use in batteries having electrolytes in liquid form and which exhibit a change in specific gravity with variations in battery charge. However, new forms of batteries have been developed which do not utilize such a liquid electrolyte but instead utilize an electrolyte or charge transfer medium which is neither liquid nor which exhibits any change in specific gravity with increasing or decreasing battery charge. These batteries include an electrolyte which are either gelular or solid in form. As a result, there is a need in the art for a battery monitor capable of monitoring the state of charge of a battery having an electrolyte which does not vary in specific gravity with variations in battery charge. Furthermore, it would be most preferable for such a monitor to be operable for monitoring the state of charge of batteries having virtually any type of electrolyte.

It is therefore the general object of the present invention to provide a new and improved battery monitor for monitoring the state of charge of a battery.

It is a more particular object of the present invention to provide such a monitor which is capable of monitoring the state of charge of a battery of the type having an electrolyte or charge transfer medium which does not exhibit a change in specific gravity with variations in battery charge.

It is a further object of the present invention to provide such a battery monitor which may be utilized in batteries of the type having a gelular or solid electrolyte.

It is a still further object of the present invention to provide such a battery monitor which may be utilized in conventional lead-acid type batteries as well.

SUMMARY OF THE INVENTION

The present invention provides a monitor for monitoring the state of charge of a battery having an internal charge transfer medium. The monitor comprises detecting means arranged to be disposed beneath the surface of the charge transfer medium and arranged for sensing the specific gravity of a fluid medium, enclosure means for enclosing the detecting means, and a fluid medium within the enclosure means. The fluid medium exhibits specific gravities related to the degree of electric charge therein and the enclosure means is formed at least partially from a non-permeable electric charge transmissible material to enable the fluid medium to assume the electric charge of the charge transfer medium while substantially separating the fluid medium therefrom. The monitor further includes indicating means responsive to the detecting means for indicating the specific gravity of the fluid medium and thus the state of charge of the battery.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIGS. 2 through 5 are front elevational views of battery monitors constructed in accordance with alternative embodiments of the present invention; and FIG. 6 is a front elevational view of a still further battery monitor embodying the present invention.

DESCRIPTION OF THE PREFERRED EMBODIMENT

Figure 1:
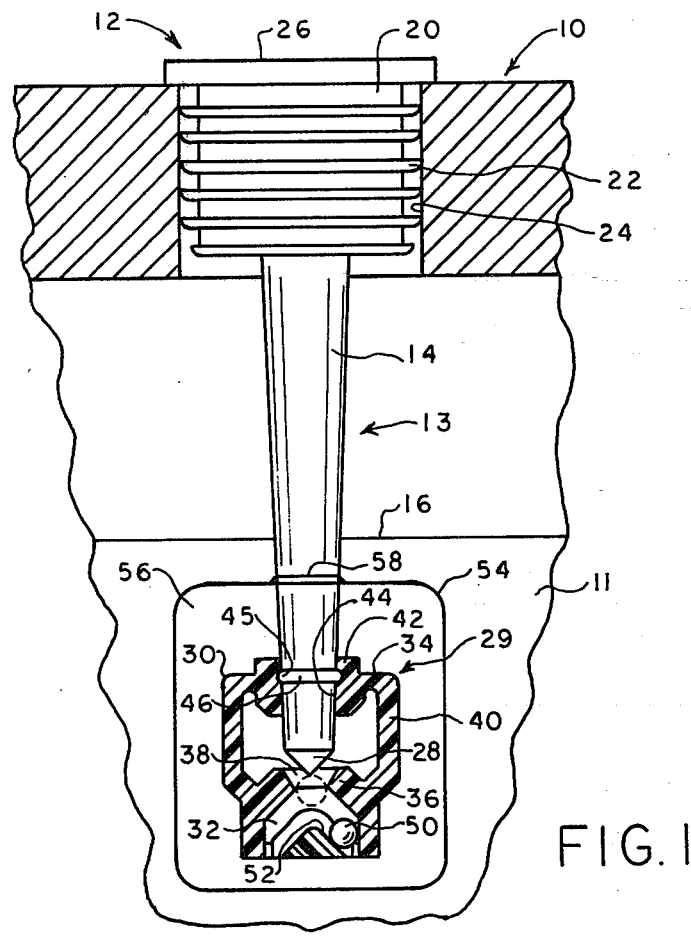
FIG. 1 is a front elevational view, partly in cross-section, of a new and improved battery monitor embodying the present invention.

Referring now to FIG. 1, a storage battery 10 is shown utilizing a state of charge battery monitor 12 embodying the present invention for monitoring the state of charge of the battery 10. The battery 10 may be of the type having an electrolyte or charge transfer medium 11 which is either gelular or solid and which does not exhibit variations in specific gravity with variations in battery charge. Also, as will be appreciated subsequently, the battery 10 may be of the conventional lead-acid type as well having a sulfuric acid electrolyte which does exhibit variations in specific gravity with variations in battery charge.

The battery monitor 12 includes an indicating means 13 in the form of a light transmissive member or rod 14 which is formed from a light transmitting material such as an acrylic, glass, styrene or other clear or partially clear materials. The rod 14 is preferably elongated so that it may be mounted in a wall of the battery or in the fluid cap of a battery with an upper end thereof exposed and a lower end thereof projecting downwardly well below the surface 16 of the electrolyte 11 within the battery 10. In this embodiment, the rod 14 is carried by a cylindrically shaped member 20 having external ribs 22 for being frictionally received in sealing relationship with a corresponding opening 24 of the battery 10. The rod 14 includes an indicating surface 26 at its upper end which is external to the battery 10 and a cone-shaped tip surface 28 which is arranged to be submerged within the electrolyte 11.

The battery monitor 12 further includes a detecting means 29 comprising a cage or chamber means 30 which is mounted at the end of the light transmissive member 14 beneath the surface 16 of the electrolyte 11. The cage 30 includes a lower chamber 32 and an upper portion 34 intergrally formed therewith. Separating the upper portion 34 from the lower chamber 32 is an upper wall 36 which is vertically inclined. Within the upper wall 36 there is provided a tapered aperture 38 which permits access of the conical tip 28 of the light transmissive member 14 to the lower chamber 32.

The light transmissive member 14 is supported and aligned with respect to the aperture 28 by a support or connecting means 40 of the upper portion 34. The support means 40 comprises a pair of upwardly extending sidewalls which include and secure a collar 42. The collar includes a through bore 44 which is in axial alignment with the aperture 38 and dimensioned for tightly receiving the light transmissive member 14 therein. In the wall of bore 44 there is provided an annular groove 45 adapted to accept a complimentary annular rib 46 carried by member 14. This arrangement insures positive assembly of member 14 and cage 30 with tip section 28 properly positioned relative to aperture 38.

The detecting means 29 is arranged to sense the specific gravity of a fluid medium and to that end, the lower chamber 32 is arranged to confine a float member or ball 50 therein. The float ball or member 50 is formed from plastic having a predetermined and known specific gravity or density and is slightly smaller in diameter than the minimum diameter dimension of the aperture 38. As will be further noted from FIG. 1, the lower chamber 32 also includes lower wall portions 52 which are substantially parallel to the upper wall portions 36. As a result, the wall portions 36 and 52 form a pair of spaced vertically inclined wall means which serve to position the float ball 50 as will be described hereinafter.

The battery monitor 12 further comprises an enclosure means 54 which totally encloses the detecting means 29. The enclosure means 54 is formed from a substantially non-permeable electric charge transmissible material. Within the enclosure means 54 there is provided a fluid medium 56. The fluid medium, preferably a dilute solution of sulfuric acid, exhibits specific gravities related to the degree of electric charge therein. The enclosure 54 is sealed to the rod 14 along a sealed interface 58 which may be formed in any well known manner such as, for example, ultrasonic welding or the like.

The enclosure 54 is preferably formed from a perfluorosulfonic acid film. One such film is currently available from E. I. duPont de Nemours & Co. under the trade name NAFION. This material is in membrane form which allows charged ions to pass therethrough but which separates the fluid medium 56 from the gelular or solid electrolyte 11. As a result, the fluid medium 56 is enabled to assume the electric charge of the charged transfer medium for electrolyte 11 while being substantially separated therefrom.

In operation, if the specific gravity of the fluid medium 56 is below a known and predetermined specific gravity, the float ball 50 will assume the position as indicated by the solid lines. In this position the float ball 50, which may preferably by red, blaze orange, green or any other desired color to facilitate viewing, will be out of view from the light transmissive member 14. Hence, the float ball 50 will not be viewable through the indicating surface 26. Because the fluid medium 56 assumes the charge of the electrolyte 11, its specific gravity will be related to the charge of the battery. In this case, since the specific gravity of the fluid 56 is below a known and predetermined specific gravity, the user will be informed that the battery is in need of recharging due to the fact that the float 50 is not viewable through the indicating surface 26.

As the battery increases in charge, the charge within the electrolyte 11 will also increase. Hence, the charge in the fluid medium 56 will correspondingly increase causing its specific gravity to increase. When the specific gravity of the fluid medium 56 is above the predetermined and known specific gravity, the float ball 50 will float upwardly and be guided by the verically inclined walls to its dashed line position. In this position, the float ball 50 is aligned with the aperture 38 and reflecting surface 28 of the light transmissive member 14, the latter blocking aperture 38, and the ball 50 will be viewable through the indicating surface 26. As a result, the user is informed that the battery is adequately charged.

In practice, it has been found that the fluid medium 56 could also take the form of water. Within a relatively short period of time, the water becomes acidic and thus is transformed to a fluid medium which exhibits specific gravities related to the charge therein. The transformation of the water to a dilute acid is believed to be caused by the charged ions flowing from the electrolyte 11, through the enclosure 54, and into the water. This provides a distinct and advantage, in that during the commercialization or manufacture of the battery monitor, assembly personnel will not be exposed to acidic solutions in providing the fluid medium 56.

Additionally, the detecting means 29 of this embodiment lends itself to remote sensing. For example, a light source and detector may be utilized within the enclosure 54 to sense when the float 50 assumes its dotted line position to provide an external indication of that fact without the need for visually sighting the indicating surface 26. Hence, the battery monitor of the present invention lends itself to be utilized in battery powered vehicles where a dashboard indicator may be employed to indicate when the battery or batteries are in need of recharging.

Figure 2:
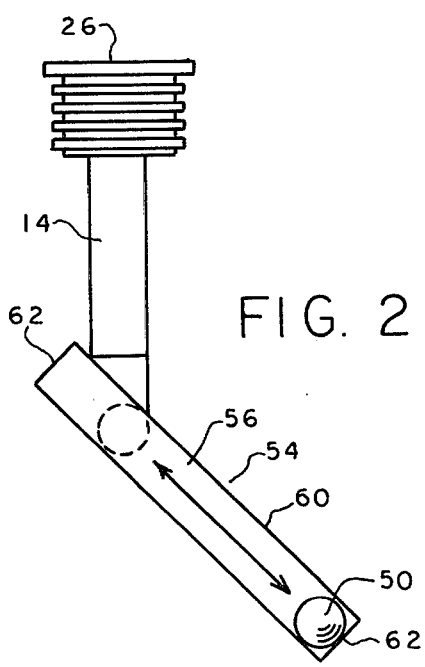

Referring now to FIG. 2, in this embodiment, the enclosure means 54 is formed at least partly from a non-permeable electric charge transmissible material of the type previously referred to. To that end, the enclosure 54 includes a glass tubular member or cylinder 60 having the non-permeable electric charge transmissible material enclosing its ends as indicated at 62. The fluid medium 56 within the enclosure 54 may once again be either a dilute solution of sulfuric acid or water which is transformed to a dilute acidic solution once employed within the electrolyte of a battery. Within the enclosure 54 is the float member 50. The float member 50 is of a known specific gravity or density and will descend within the enclosure 54 from its dashed line position indicating adequate charge to its solid line position out of view through the indicating surface 26 indicating the need for recharging when the specific gravity of the fluid medium 56 falls below the predetermined and known specific gravity.

The cylindrical member 60 of this embodiment need not necessarily be formed from glass. It can just as well be formed from any suitable insulating material which is not attacked by the electrolyte into which it is to be placed.

Figure 3:
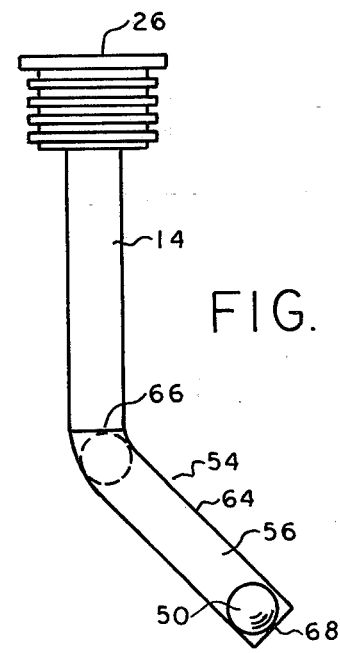

The embodiment of FIG. 3 is similar to the embodiment of FIG. 2 in that the enclosure 54 once again takes the form of a hollow cylinder 64. Here, one end 66 of the cylinder is terminated by the rod number 14 and the other end is enclosed by the aforementioned membrane material 68. Again, the non-permeable electric charge transmissible material 68 permits the fluid medium 56 within the cylinder 64 to assume the charge of the electrolyte into which the cylinder 64 is placed. As a result, the float ball 50 will move between its dashed line position to its solid line position when the battery, into which it is placed, is discharged. Again, the monitor of FIG. 3 includes the viewing surface 26 whereat the float member 50 may be seen when in its dashed line position indicating adequate battery charge.

Referring now to FIG. 4, the battery monitor of this embodiment is essentially identical to the battery monitor of FIG. 2 except that the cylinder 60 is enclosed by metallic caps 70. The caps 70 may be formed from stainless steel, brass, or any other conducting material. The metallic caps 70 will thereby provide a non-permeable electric charge transmissible material separating the fluid medium 56 within the cylinder 60 from the surrounding electrolyte of the battery into which the cylinder 60 is placed.

Because the end caps 70 are formed from a conducting material, the charge within the electrolyte will be transmitted through the end caps 70 to enable the fluid medium 56 to assume the charge of the electrolyte. As a result, the battery monitor of FIG. 4 will function in the same manner as that of FIG. 2 with the float member 50 descending from its dashed line position to its solid line position when the battery is in need of charge.

In FIG. 5, this embodiment is substantially similar to that of FIG. 3 except that the cylinder 64 is enclosed by a metallic end cap 70. Again, the battery monitor of FIG. 5 functions in the same manner as the battery monitor of FIG. 3 with the float member 50 descending to its solid line position from its dashed line position as the battery becomes discharged. When in the dashed line position, the float member 50 will be clearly visible through the indicating surface 26.

Referring now to FIG. 6, in this embodiment, the battery monitor once again includes a cylindrical enclosure 72 formed form insulating material. The hollow cylinder 72 is enclosed by end members 74 which may be either the previously referred to membrane material, or, conductive end caps. As with the previous embodiments, a fluid medium 56 is introduced into the cylinder 72.

A pair of float members 76 and 78 are provided with each float member having a different color. For example, float member 78 may be green, and float member 76 may be red. The rod member 14 intersects and partially enters the cylinder 72. Along opposed sides of the rod 14 there are provided arcuate cut out sections 80 and 82 having a radius of curvature in portions thereof approximating the radius of curvature of the float members 76 and 78.

When the fluid medium 56 within the cylinder 72 has a specific gravity which is below the known and predetermined specific gravity due to the charge therein which is also the charge of the electrolyte, the float member 76 will be in contact with the arcuate surface 80 and thus viewable through the indicating surface 26. The other float member 78 will be out of view as illustrated. As a result, the user will see a red float member through the indicating surface 26 to thereby be informed that the battery in which the monitor is utilized is in need of recharging.

As long as the battery charge is adequate, the charge within the electrolyte and thus the charge within the fluid medium 56 will be such that the fluid medium 56 will have a specific gravity which is above the known and predetermined specific gravity. The float member 76 will be at the top of the cylinder 72 and the other float member 78 will be in contact with the arcuate surface 82. Hence, the green float member 78, now viewable through the indicating surface 26, informs the user that the battery is not in need of recharging.

While specific embodiments of the present invention have been shown and described, modifications may be made, and it is therefore intended to cover in the appended claims all such changes and modifications which fall within the true spirit and scope of the invention as defined by said claims.

I claim:

1. A monitor for monitoring the state of charge of a battery having an internal charge transfer medium comprising: detecting means arranged to be disposed beneath the surface of said charge transfer medium and arranged for sensing the specific gravity of a fluid medium; enclosure means for enclosing said detecting means; a fluid medium within said enclosure means, said fluid medium exhibiting specific gravities related to the degree of electric charge therein, said enclosure means being formed at least partly from a non-permeable electric charge transmissible material to enable said fluid medium to assume the electric charge of said charge transfer medium while substantially separating said fluid medium therefrom; and indicating means responsive to said detecting means for indicating the specific gravity of said fluid medium and thus the state of charge of the battery.

2. A monitor as defined in claim 1 wherein said detecting means comprises a float of a predetermined density arranged to assume a plurality of positions within said enclosure means responsive to the specific gravity of said fluid medium.

3. A monitor as defined in claim 2 wherein said indicating means includes means for indicating the position of said float for indicating the specific gravity of said fluid medium and thus the state of charge of the battery.

4. A monitor as defined in claim 3 wherein said indicating means comprises a light transmissive member having a first end aligned with said enclosure means and a second end external to the battery having a viewing surface to permit visual observation of the position of said float within said enclosure means.

5. A monitor as defined in claim 1 wherein said non-permeable electric charge transmissible material comprises a perfluorosulfonic acid film.

6. A monitor as defined in claim 1 wherein said non-permeable electric charge transmissible material comprises metallic material.

7. A monitor as defined in claim 1 wherein said enclosure means comprises a hollow cylindrical portion formed of electrical insulating material having a closure cap enclosing at least one end thereof formed from said non-permeable electric charge transmissible material.

8. A monitor as defined in claim 7 wherein said closure cap comprises a perfluorosulfonic acid film.

9. A monitor as defined in claim 7 wherein said closure cap is formed from metallic material.

10. A monitor as defined in claim 7 wherein said detecting means comprises a ball-shaped float member having a predetermined density arranged to move within said cylindrical portion responsive to the specific gravity of said fluid medium.

11. A monitor as defined in claim 1 wherein said fluid medium comprises a dilute solution of sulfuric acid.

12. A monitor as defined in claim 1 wherein said enclosure means comprises a hollow tubular member formed from electrically insulating material enclosed at its ends by said non-permeable electric charge transmissive material, wherein said indicating means comprises a light transmissive member intersecting and partially entering said enclosure at a first end thereof and having a viewing surface at the other end wherein said light transmissible member and said tubular member are angularly disposed with respect to each other, and wherein said detecting means comprises a pair of float members on opposite sides of said light transmissible member, said float members being of substantially equal density and of a different color so that when the battery is charged to a predetermined level one of said float members is viewable through said viewing surface and when the battery is charged below said predetermined level the other said float member is viewable through said viewing surface.

13. A monitor for monitoring the state of charge of a battery of the type having an electrolyte which maintains a substantially constant specific gravity notwithstanding variations in the state of charge of the battery, said monitor comprising: an enclosure within the electrolyte defining a cavity, said enclosure being at least partially formed from a substantially non-permeable charge transmissible material; a fluid medium within said cavity, said fluid medium comprising a material which exhibits a varying specific gravity responsive to the charge therein and arranged to assume therein the charge of the battery electrolyte by the passage of charge from the electrolyte through said substantially non-permeable charge transmissable material while being substantially separated from the electrolyte; specific gravity detecting means immersed within said fluid medium for sensing the specific gravity of said fluid medium and thus the state of charge of the battery; and indicating means coupled to said detecting means for providing an indication of the state of charge of the battery responsive to said detecting means.

14. A monitor as defined in claim 13 wherein said fluid medium comprises a liquid.

15. A monitor as defined in claim 14 wherein said liquid comprises a dilute acid solution.

16. A monitor as defined in claim 13 wherein said substantially non-permeable charge transmissible material comprises a perfluorosulfonic acid film.

17. A monitor as defined in claim 16 wherein said enclosure is entirely formed from said perfluorosulfonic acid film.

18. A monitor as defined in claim 13 wherein said substantially non-permeable charge transmissible material comprises metallic material.

19. A monitor as defined in claim 13 wherein said detecting means comprises a float member having a predetermined density and wherein said float member is adapted to change position within said enclosure reponsive to the specific gravity of said fluid medium.

20. A monitor as defined in claim 19 wherein said indicating means includes means for indicating the position of said float member within said enclosure.

* * * * *